(12) United States Patent
Tasaki et al.

(10) Patent No.: US 8,220,717 B2
(45) Date of Patent: Jul. 17, 2012

(54) TUBULAR CONTAINER ENABLING INDIVIDUAL IDENTIFICATION

(75) Inventors: Kouji Tasaki, Chikusei (JP); Hironori Ishizaka, Yuki (JP); Hisayo Masuda, Yuki (JP); Susumu Yamada, Yokohama (JP)

(73) Assignee: Hitachi Chemical Co., Ltd., Tokyo (JP)

( * ) Notice: Subject to any disclaimer, the term of this patent is extended or adjusted under 35 U.S.C. 154(b) by 445 days.

(21) Appl. No.: 12/159,997

(22) PCT Filed: Jan. 5, 2007

(86) PCT No.: PCT/JP2007/050028
§ 371 (c)(1),
(2), (4) Date: Sep. 18, 2009

(87) PCT Pub. No.: WO2007/077996
PCT Pub. Date: Jul. 12, 2007

(65) Prior Publication Data
US 2010/0032486 A1    Feb. 11, 2010

(30) Foreign Application Priority Data
Jan. 5, 2006  (JP) ................... P2006-000683

(51) Int. Cl.
*G06K 19/06* (2006.01)
*G06K 7/08* (2006.01)
(52) U.S. Cl. ...... 235/492; 235/375; 235/451; 340/572.1
(58) Field of Classification Search .......... 235/375, 235/380, 451, 492; 340/572.1, 572.2, 572.7, 340/10.1, 10.2; 705/2, 3
See application file for complete search history.

(56) References Cited

U.S. PATENT DOCUMENTS

| 5,731,957 | A | 3/1998 | Brennan |
| 6,137,413 | A | 10/2000 | Ryan, Jr. |
| 6,216,647 | B1 * | 4/2001 | Bailey ................ 123/46 R |
| 6,230,935 | B1 * | 5/2001 | Mack et al. ............ 222/137 |
| 6,657,542 | B2 | 12/2003 | Usami |
| 6,859,745 | B2 | 2/2005 | Carr et al. |
| 7,034,689 | B2 * | 4/2006 | Teplitxky et al. ....... 340/572.7 |
| 7,275,682 | B2 * | 10/2007 | Excoffier et al. .......... 235/375 |

(Continued)

FOREIGN PATENT DOCUMENTS

EP    0 364 045 A1    4/1990

(Continued)

OTHER PUBLICATIONS

Extended European Search Report; Supplementary European Search Report and European Search Opinion; Application No. EP 07 70 6375 dated Feb. 18, 2010.

(Continued)

*Primary Examiner* — Tuyen K Vo
(74) *Attorney, Agent, or Firm* — Antonelli, Terry, Stout & Kraus, LLP.

(57) ABSTRACT

A tubular container enabling individual identification, suitable to store semen of a domestic animal or a small amount of an organism individual sample and to manage history information, excellent in reliability, workability, and communication characteristics, and incorporating an IC tag. The tubular container is composed of a resin tubular container, a sealing cap, an IC tag embedded in the sealing cap and composed of an IC chip and a first transmitting/receiving antenna, and a second transmitting/receiving antenna fixed to the tubular container.

21 Claims, 4 Drawing Sheets

U.S. PATENT DOCUMENTS

| | | | |
|---|---|---|---|
| 7,696,886 B2 * | 4/2010 | Lai | 340/572.7 |
| 2004/0008123 A1 * | 1/2004 | Carrender et al. | 340/825.49 |
| 2004/0115096 A1 * | 6/2004 | Itoh | 422/99 |
| 2005/0064579 A1 * | 3/2005 | Loskutoff et al. | 435/283.1 |
| 2007/0013521 A1 * | 1/2007 | Lindsay et al. | 340/572.1 |
| 2007/0069037 A1 * | 3/2007 | Kawai | 235/492 |
| 2007/0075141 A1 * | 4/2007 | Veitch et al. | 235/435 |
| 2008/0149584 A1 * | 6/2008 | Martinelli | 215/201 |

FOREIGN PATENT DOCUMENTS

| | | |
|---|---|---|
| JP | 07-042514 | 8/1995 |
| JP | 08-048337 | 2/1996 |
| JP | 08-211065 | 8/1996 |
| JP | 2000-137779 | 5/2000 |
| JP | 2000-510271 | 8/2000 |
| JP | 2000-322542 | 11/2000 |
| JP | 2001-356688 | 12/2001 |
| JP | 2002-042078 | 2/2002 |
| JP | 2002-259934 | 9/2002 |
| JP | 2002-529320 | 9/2002 |
| JP | 2003-179526 | 6/2003 |
| JP | 2004-139535 | 5/2004 |
| JP | 2004-336604 | 11/2004 |
| JP | 2004-535336 | 11/2004 |
| JP | 2005-222452 | 8/2005 |
| JP | 2005-321935 | 11/2005 |
| JP | 2005-339170 | 12/2005 |
| JP | 2005-348197 | 12/2005 |
| JP | 2006-195796 | 7/2006 |
| TW | 577026 | 2/2004 |
| TW | M259278 | 3/2005 |
| WO | WO 02/095671 | 11/2002 |
| WO | WO 2005/055120 | 6/2005 |
| WO | WO 2005/059815 | 6/2005 |
| WO | WO 2005/119585 | 12/2005 |

OTHER PUBLICATIONS

Taiwanese Official Action issued Mar. 29, 2010, for Application No. 096100562.

"Frozen bovine semen inventory managed with wireless IC tag", Prefectural Livestock Research Institute, Morning Ed., Gifu Area, p. 18, Oct. 13, 2005.

Japanese Official Action dated Jul. 5, 2011, for JP Application No. 2007-553005.

Japanese Official Action dated Nov. 8, 2011, for JP Application No. 2007-553005.

* cited by examiner

TUBULAR CONTAINER ENABLING INDIVIDUAL IDENTIFICATION

TECHNICAL FIELD

The present invention relates to a tubular container enabling individual identification.

BACKGROUND ART

In recent years problems with bovine spongiform encephalopathy (BSE) and deceptive symptoms have occurred affecting the meat production industry. Systems are required to enable producers, meat processors and distributors to guarantee the safety of their products and to construct information management systems that enable safe products to be supplied to consumers.

The breeding of cattle and pigs etc. is mainly facilitated using artificial insemination employing semen obtained from breeding stock bulls and pigs and bloodline management is essential in order to maintain safety and product quality. Normally, seminal fluid from breeding stock bulls and pigs is apportioned in thin, tubular containers which are then subject to cool storage and when artificial insemination takes place the required number of these tubular containers are removed from a cool store vehicle. A lot of work goes into handling the information for identifying large volumes of these tubular containers, ascertaining when and from which animals the seminal fluid was acquired and then tracing the exact routes showing the processing and distribution of the domestic animals resulting from the breeding through to the products being delivered to consumers. Throughout these processes errors frequently occur.

Noncontact IC tags play an important role in these identification and management procedures. Noncontact IC tags are electronic devices that enable a variety of information to be written to or read from an IC chip using wireless transmission so that the information can be stored in a computer, managed and supplied to different people over a computer network. If for example an IC tag is affixed to a tubular container in advance it becomes possible to accurately manage the history information and identification of that container from the point in time at which seminal fluid is put into the container.

At the Gifu Prefectural Livestock Research Institute a traceability system has been developed for managing history information on production and distribution that enables management and tracing of cattle blood lines back to the stage of artificial insemination, by storage and management of frozen seminal fluid used for artificial insemination using tubular containers having a wireless IC tag attached. Usage of the system has commenced on an experimental basis (refer Oct. 13, 2005 edition of the Chunichi Shimbun).

The containers used for storing seminal fluid of domestic animals usually consist of a plastic container of about 2-3 mm in diameter, about 10-15 cm long of a tubular shape having a cotton plug at one end. An IC tag is attached at one end of the tubular container however this must be a small member of less than a few centimeters in order to ensure that the tag does not inhibit work and storage functions.

Wireless transmission technology is used in these noncontact IC tags. The international standard is that the operating frequency for such transmission is 13.56 MHz, 860-960 MHz or 2.45 GHz. The operation of the IC tag varies according to the frequency used and the features of a tag differ according to the size and transmission capabilities etc., however a relatively small size can be achieved for an IC tag operating in the 2.45 GHz band.

The aim however is to achieve satisfactory transmission capabilities in a tag of about 5 cm long, as there are concerns that a tag attached to the outside of a tubular container may obstruct handling of the container, while it must be able to withstand storage for a long time and be mechanically robust.

FIG. 1 shows an example of a tubular container with an IC tag attached on the outside. An IC tag 20 comprised of an IC chip 21 and a transmitting/receiving antenna 22 is attached on the surface of a tubular container 1. Seminal fluid of a domestic animal is inserted into the container from the end opposite the end having a cotton plug 6. After the seminal fluid is put into the container the end is sealed, before storage, either by thermal sealing or ultrasonic waves.

FIG. 2 shows another example of a tubular container with an IC tag attached on the outside. As the container end is sealed after seminal fluid is put inside the container the end of the IC tag 20 is secured inserted inside the end of the container.

In both configurations shown in FIG. 1 and FIG. 2 however there is concern that if the IC tag attached to the outside of the tubular container is subject to obstruction during handling pressure may be applied on the IC tag from the outside causing damage.

Tasaki et al., the inventors of the present invention, have already submitted a miniature IC tag of 4 mm×3 mm (Japanese Patent Application Laid-Open No. 2005-007583). In the case of this miniature IC tag however, it can be placed inside a tubular container, although as the radio wave transmission efficiency of the miniature antenna is poor the distance of transmission between the IC tag and the reading device is very limited leading to inferior read capabilities during processing.

The problems are not restricted to containers used for storing domestic animal semen. In recent years with the rapid advancement in biotechnology the same issues have arisen in the handling of large numbers of individual samples of different organisms. A system is required that enables storage and accurate history management of such samples.

DISCLOSURE OF THE INVENTION

Problems to be Solved by the Invention

Against this background, the present invention provides a tubular container that incorporates an IC tag and enables identification of an individual, that is suitable for storing and managing history information of seminal fluid of a domestic animal or a small amount of sample material of an individual organism, is highly reliable, withstands work procedures very well and has excellent communications properties.

Means for Solving the Problem

The present invention is a tubular container suitable for storing and managing history information of seminal fluid of a domestic animal or a small amount of sample material of an individual organism, providing an IC tag embedded in the sealing cap of the tubular container and further providing a first transmitting/receiving antenna, and a second transmitting/receiving antenna separated from the IC tag fixed in the tubular container.

Because the IC tag is embedded in the sealing cap the tag is highly reliable and mechanically robust, and withstands work procedures very well.

Further, even though the first transmitting/receiving antenna and the second transmitting/receiving antenna are not electrically connected an electrical coupling arises due to static electricity occurring between these two antennas when a high frequency electric current is transmitted or received, and even though the first transmitting/receiving antenna attached to the IC chip is extremely small, satisfactory transmission capabilities are realized due to the contribution of the second transmitting/receiving antenna.

That is to say the present invention is as follows.

The tubular container that enables identification of an individual is a tubular container that has an IC tag for individual identification, comprising a tubular container of resin, a sealing cap, an IC tag embedded in the sealing cap and further comprising an IC chip and a first transmitting/receiving antenna and a second transmitting/receiving antenna fixed to the tubular container.

It is preferable that in the tubular container enabling individual identification according to the present invention, the IC tag should have a maximum length of 15 mm.

It is preferable that in the tubular container enabling individual identification according to the present invention, the length of the second transmitting/receiving antenna is within a range of 30 mm-60 mm.

It is preferable that in the tubular container enabling individual identification according to the present invention, the second transmitting/receiving antenna is a metallic film fixed to the tubular container.

It is preferable that in the tubular container enabling individual identification according to the present invention, the second transmitting/receiving antenna is a metallic wire fixed to the tubular container.

It is preferable that in the tubular container enabling individual identification according to the present invention, the second transmitting/receiving antenna is a conductive, hardened paste formed on the surface of the tubular container.

It is preferable that in the tubular container enabling individual identification according to the present invention, the sealing cap is comprised of a fiber part and a powder part.

It is preferable that in the tubular container enabling individual identification according to the present invention, that the sealing cap is a foam resin.

It is preferable that in the tubular container enabling individual identification according to the present invention, that the outer diameter of the tubular container be not more than 3 mm.

It is preferable that in the tubular container enabling individual identification according to the present invention, that the material from which the tubular container is made is any from among polyvinyl chloride resin, polypropylene resin, polyethylene resin or polyester resin.

It is preferable that in the tubular container enabling individual identification according to the present invention, the IC tag operates on a carrier wave of 2.45 GHz.

It is preferable that in the tubular container enabling individual identification according to the present invention, the IC tag comprises an IC chip having an external electrode formed on each surface of the pair of facing surfaces, a first transmitting/receiving antenna having a T-shaped slit formed therein, and a short circuit board electrically connecting the IC chips and the first transmitting/receiving antenna.

It is preferable that the tubular container enabling individual identification according to the present invention be stored in liquid nitrogen.

It is preferable that liquid stored in the tubular container enabling individual identification according to the present invention be the seminal fluid of a domestic animal.

It is preferable that the tubular container enabling individual identification according to the present invention has a third transmitting/receiving antenna fixed to the tubular container.

Effects of the Invention

The tubular container incorporating an IC tag according to the present invention furnishes the following effects.

By employing a tubular container comprising an IC tag that is embedded in the sealing cap and comprises an IC chip and a first transmitting/receiving antenna, as well as a second transmitting/receiving antenna fixed to the tubular container, a tubular container that incorporates an IC tag is realized, that is suitable for storing and managing history information of seminal fluid of a domestic animal or a small amount of sample material of an individual organism, is highly reliable, withstands work procedures very well and has excellent communications properties.

BEST MODE FOR CARRYING OUT THE INVENTION

The tubular container providing an IC tag for individual identification according to the present invention comprises a tubular container of a resinous material, a sealing cap, an IC tag, which is embedded in the sealing cap and further comprises an IC chip and a first transmitting/receiving antenna, and a second transmitting/receiving antenna fixed to the tubular container.

The embodiments of the present invention will now be described with reference to the drawings, it being understood that the following description is provided for illustrative purposes only and it is not intended that the invention should be limited by the following embodiments as described.

Figure 1:
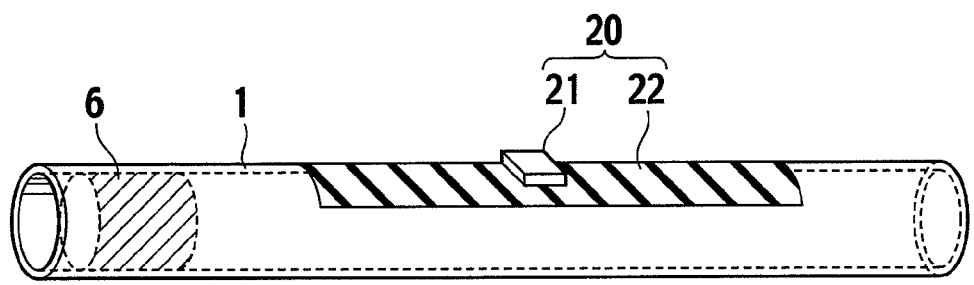
FIG. 1 provides a schematic illustration of an example of a conventional tubular container with IC tag attached.
Figure 2:
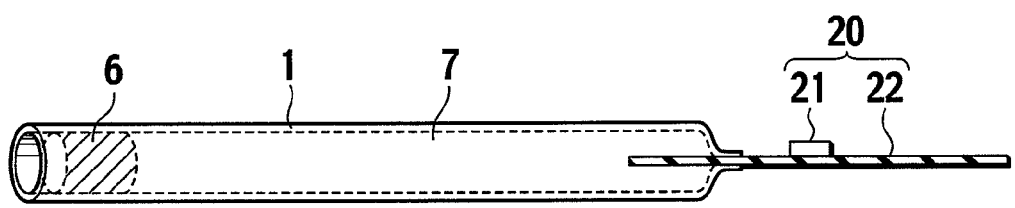
FIG. 2 provides a schematic illustration of an example of a conventional tubular container with IC tag attached.
Figure 3:
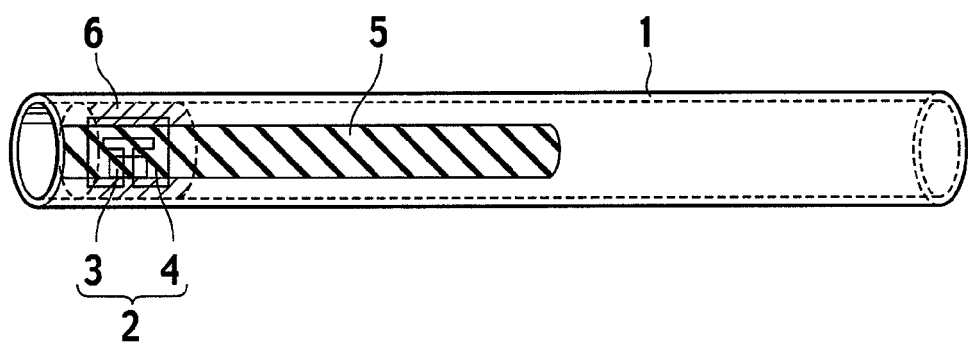
FIG. 3 provides a side view of an example of a tubular container with IC tag attached according to the present invention.

FIG. 3 provides a side view of an example of a tubular container with IC tag attached according to the present invention.

Here, the invention comprises an IC tag 2 comprising an IC chip 3, and a first transmitting/receiving antenna 4 embedded inside a sealing cap 6 at one and of a tubular container 1 comprised of a resinous material, and a second transmitting/receiving antenna 5 separate to the IC tag 2, that is formed on the surface of the tubular container 1.

This second transmitting/receiving antenna can be either a thin metallic film, a metallic wire or a conductive, hardened paste.

If the second transmitting/receiving antenna 5 is of metallic film or metallic wire, then where the tubular container 1 is formed of a heat transmissible resin, it can be applied either by directly welding its to the surface of the container or by adhering it to the surface using an adhesive.

Further, when the tubular container 1 is produced by molding processes the metallic film or metallic wire can be formed integrally with the container.

If a conductive paste is used for the second transmitting/receiving antenna 5, the antenna can be formed by hardening the substance on the surface of the tubular container 1 after the substance is painted or printed onto the surface.

For a conductive paste a paste containing either silver or bronze flakes provides good electrical conductivity and satisfactory communications properties.

For the IC tag 2 a variety of different operating frequencies exist according to the principles of operation and international standards and any of these frequencies is suitable. However as it is desirable that the IC tag 2 be of miniature form as it will be embedded in the sealing 6 of the tubular container 1, then in the 13.56 MHz, 860-960 MHz and 2.45 GHz bands that are normally used, a coil form transmitting/receiving antenna is not suitable, while an IC tag 2 that uses the 2.45 GHz band in which the frequency is long and the wavelength short, is most suitable for realizing a miniature form.

Further, it is desirable that the sealing cap 6 of the tubular container 1 be of small form in order to maintain sufficient packing capacity with respect to the liquid body in the container. Accordingly, as an example of the tubular container 1 containing seminal fluid of a domestic animal, a container actually realized so far consists of a total length of approximately 120 mm and a sealing cap part length of approximately 15 mm, this sealing cap 6 being configured having a powder containing part of approximately 3 mm in length with parts consisting of fiber on either side thereof of approximately 5 mm in length. Thus an IC tag 2 of not more than 15 mm in length is satisfactory, while a length of not more than 10 mm is more preferable as this enables the end of the IC tag 2 to be completely embedded in the sealing cap 6, while a length of 3 mm is most preferable to enable the powder containing part to be embedded in the sealing cap 6.

When a 2.45 GHz band IC tag 2 is selected an antenna that is a half wavelength dipolar antenna is satisfactory for enabling efficient transmission/reception of radio waves. A half wavelength of 2.45 GHz radio waves is approximately 120 mm, but as the transmission/reception capability diminishes as the antenna becomes shorter, the preferred length for the second transmitting/receiving antenna 5 secured to the tubular container is from 30 mm-60 mm.

Figure 4:
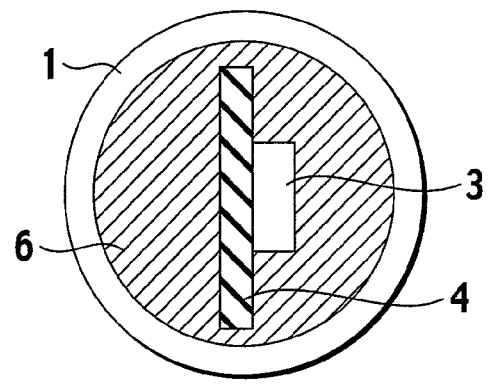
FIG. 4 provides a schematic view of an example of the IC tag embedded part of a tubular container with IC tag attached according to the present invention.

FIG. 4 shows an example of the sealing cap 6 and IC tag 2 embedded part. This shows the IC tag 2 embedded inside a uniform sealing cap 6. The sealing cap 6 can be made from a fiber that is woven material, nonwoven material or a knitted fabric while the foam resin can be polyethylene, polyester or polyurethane.

Figure 5:
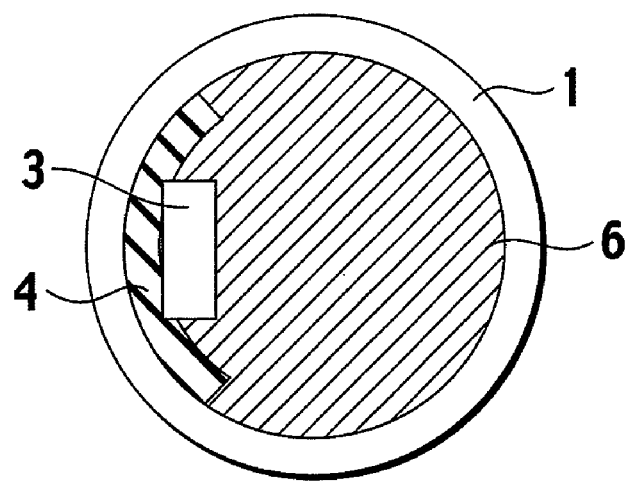
FIG. 5 provides a schematic view of an example of the IC tag embedded part of a tubular container with IC tag attached according to the present invention.

FIG. 5 shows another example of the sealing cap 6 and IC tag 2 embedded part. This shows the case in which the IC tag 2 is embedded in the opening between the sealing cap 6 in the tubular container 1. In the same manner as the case shown in FIG. 4, the sealing cap 6 can be made for example of woven material, nonwoven material or knitted fabric, while the foam resin can be polyethylene, polyester or polyurethane.

Figure 6:
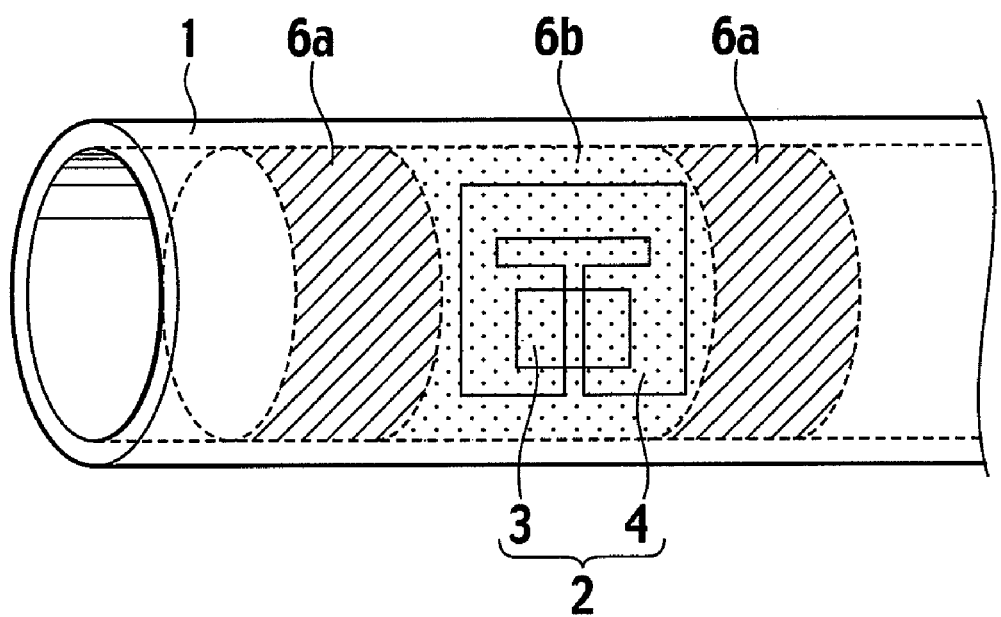
FIG. 6 provides a schematic view of an example of the IC tag embedded part of a tubular container with IC tag attached according to the present invention.

FIG. 6 shows another example of the sealing cap 6 and IC tag 2 embedded part. Here, the sealing cap 6 comprises a fabric part 6a that is a knitted fabric, woven or nonwoven material and a powder part 6b, while the IC tag 2 is embedded in the powder part 6b.

The tubular container 1 can be made from a nonmetallic material, and from a cost and ease-of-processing viewpoint, polyvinyl chloride resin, polypropylene resin, polyethylene resin or polyester resin are most suitable.

As described above, the following can be considered as a suitable example of IC tag configuration for enabling an IC tag 2 of the length of 3 mm-15 mm to be embedded in the sealing cap 6.

Firstly, an extremely small chip of 0.4 mm×0.4 mm, called μ-Chip by Hitachi provides the IC chip 3.

Figure 7:
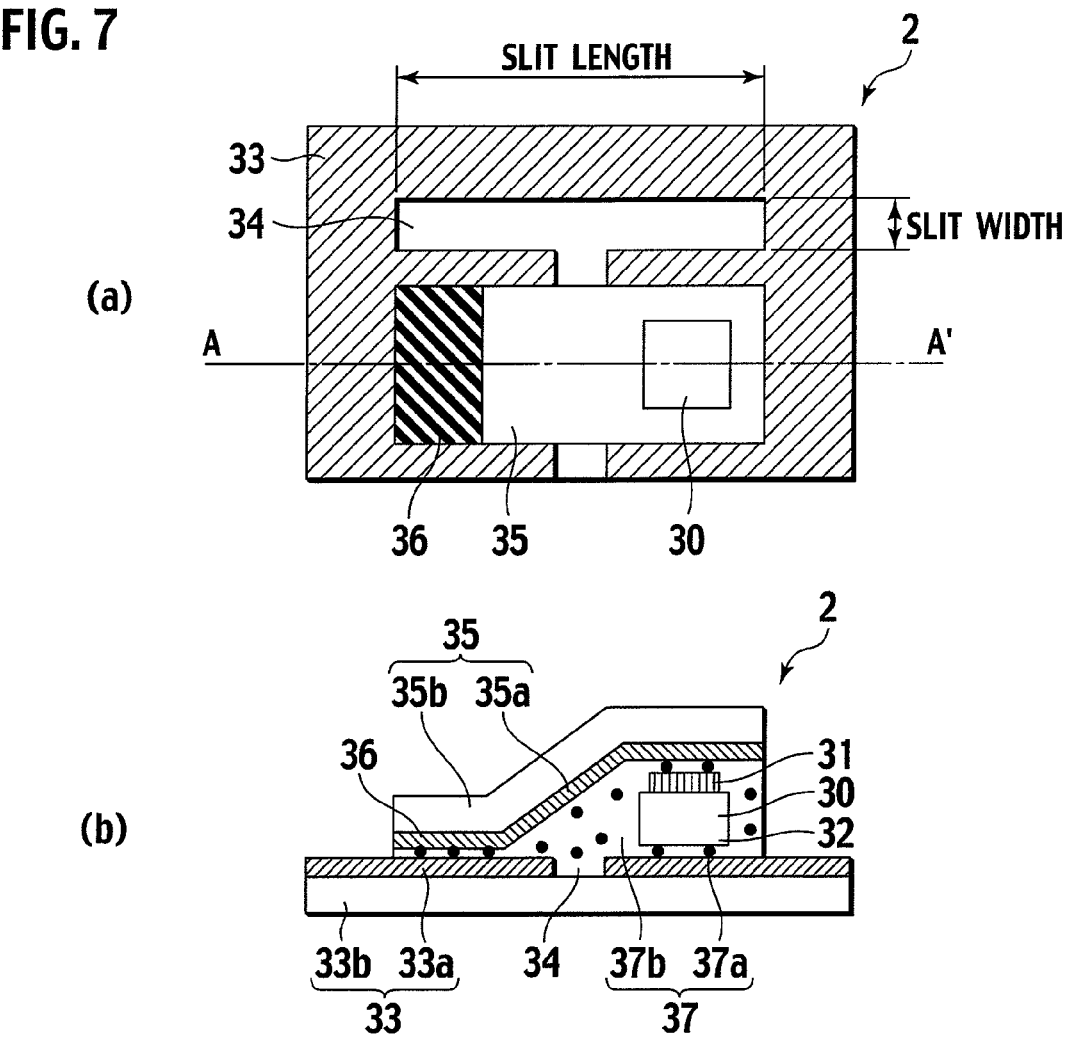
FIG. 7 provides FIG. 7 (a) showing a schematic illustration of an example of an IC tag configuration suitable for the present invention, FIG. 7 (b) showing a cross-section along the line A-A' in FIG. 7 (a)

Next, as a mounting structure for the IC chip 3, the most suitable structure for realizing a small sized configuration employs a short circuit board electrically connecting an IC chip having two external electrodes, one each formed on the front and reverse surfaces (hereinafter "both-sided electrodes IC chip") and a transmitting/receiving antenna having a T-shaped slit. FIG. 7 shows a schematic view of this mounting configuration.

FIG. 7 (a) provides a schematic view from above, of the IC tag 2. A T-shaped slit 34 is formed in the transmitting/receiving antenna 33 the lengthwise length of which is 3 mm-10 mm. By altering the width of this slit 34 within the range of 0.2 mm-0.7 mm or the length within the range of 2.0-3.0 mm it is possible to adjust the impedance between the transmitting/receiving antenna 33 and the both-sided electrodes chip 30. With the slit 34 residing between, the external electrode on one side of the both-sided electrodes chip 30 makes contact with the transmitting/receiving antenna 33, while the external electrode on the side opposite that side in contact with the transmitting/receiving antenna 33 contacts the short circuit part 36 on the opposite side of the slit 34 via the short circuit board 35.

FIG. 7 (b) shows a cross-section along the line A-A'. The both-sided electrodes chip 30 comprises the external electrode 31 formed over a circuit comprised of semiconductor elements and the external electrode 32 that uses the base substrate surface itself. The external electrode 32 on one side of the both-sided electrodes chip 30 and the transmitting/receiving antenna 33 are connected via an anisotropic conductive adhesive agent 37. The external electrode 31 on the other side of the both-sided electrodes chip 30 and the short circuit board 35 are connected via that anisotropic conductive adhesive agent 37, as are also the short circuit board 35 and the transmitting/receiving antenna 33 at the opposite side with the slit 34 lying between them and the both-sided electrodes 30.

In FIG. 7 (b), the transmitting/receiving antenna 33 comprises the metallic film antenna 33a and a carrier film 33b holding it, the short circuit board 35 comprises a metallic film 35a and a carrier film 35b holding that, while the anisotropic conductive adhesive agent 37 comprises conductive particles 37a and a matrix resin 37b.

Generally, in order to adjust the impedance between the IC chip 3 and transmitting/receiving antenna the inductance and capacitance is adjusted by a slit formed in the transmitting/receiving antenna, but when the mounting configuration shown in FIG. 7 is used, contributing inductance and capacitance arises from the short circuit board 35, and the length of the slit 34 can be shortened which is conducive to formation of an IC chip 2 of not more than 10 mm long.

Where the tubular container 1 according to the present invention is used, in which the IC tag 2 is embedded in the sealing cap 6, the problems of the IC tag 2 protruding outside of the container and of inferior reliability and mechanical strength as well as inferior ability to withstand handling that effect tubular containers with IC tags attached according to the conventional art do not arise.

Moreover, even when seminal fluid of a domestic animal for example is stored at an extremely low temperature in liquid nitrogen for example (−196° C.), the problems of rapid temperature change or condensation on the IC tag 2 after removal from the extremely low temperature leading to poor readability do not arise because of the protection provided by the sealing cap 6.

Figure 8:
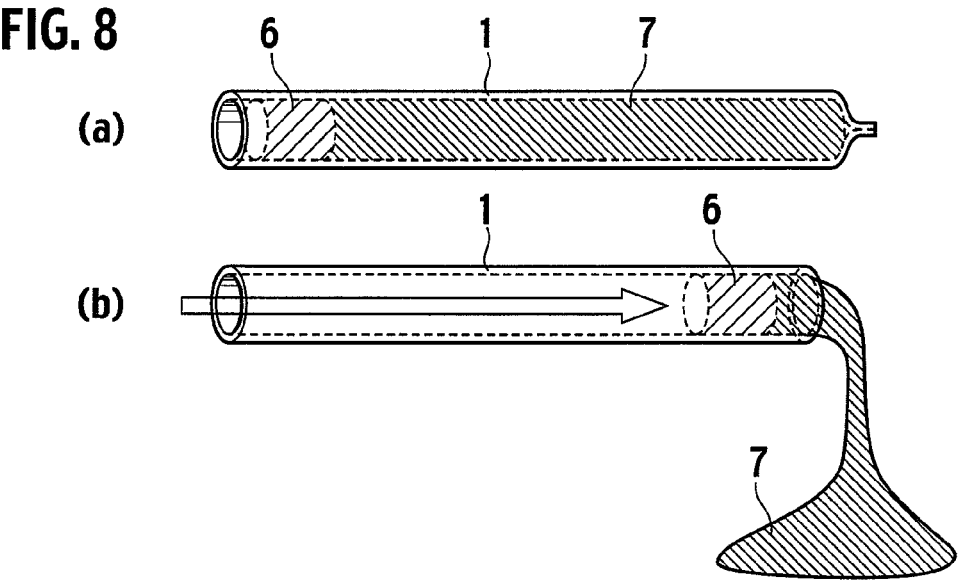
FIG. 8 provides FIG. 8 (a) showing a schematic illustration depicting an example of the usage of the tubular container with IC tag attached according to the present invention, FIG. 8 (b) showing a schematic illustration depicting an example of the usage of the tubular container with IC tag attached according to the present invention.

When the seminal fluid is to be stored, as shown in FIG. 8(*a*), after the tubular container 1 is filled with the seminal fluid 7 one end of the tubular container 1 is tightly fuse sealed. When the seminal fluid is used, as shown in FIG. 8(*b*), the sealed end is cut off and the sealing cap 6 is pushed into the tubular container 1 from the outside to release the seminal fluid 7.

As described above because it is preferable that the length of the tubular container 1 is 120 mm and the length of the second transmitting/receiving antenna 5 fixed to the tubular container 1 is 30 mm-60 mm, it is conceivable that after the sealing cap 6 is pushed in the second transmitting/receiving antenna 5 may become incapable of contributing to transmission with the IC tag 2.

Figure 9:
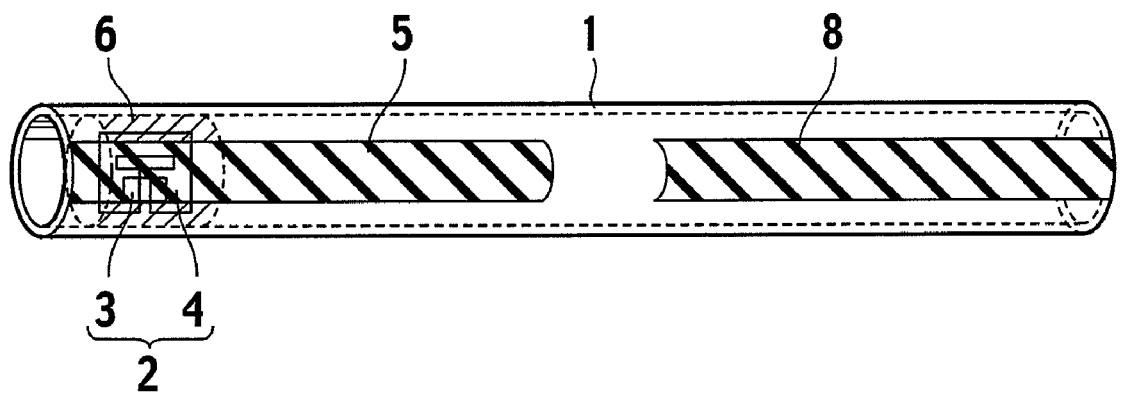
FIG. 9 provides a side view showing an example of the tubular container with IC tag attached according to the present invention.

Accordingly, when it is deemed necessary that satisfactory transmission with the IC tag 2 must be possible not only after storage and before use but after use also, it is beneficial to have a third transmitting/receiving antenna 3 fixed to the tubular container that can contribute to transmission when the sealing cap 6 is in the position it takes after being pushed into the container. FIG. 9 shows an example of a tubular container 1 with a third transmitting/receiving antenna formed. The third transmitting/receiving antenna 8 forms an electromagnetic coupling by static electricity with the first transmitting/receiving antenna 4 of the IC tag 2 when the third transmitting/receiving antenna 8 of the IC tag 2 approaches as the sealing cap 6 is pushed inwards. Because of this, even when the first transmitting/receiving antenna 4 is extremely small satisfactory transmission capabilities are maintained due to the contribution from the third transmitting/receiving antenna 8.

EMBODIMENTS

Exemplary embodiments of the invention will now be described below. The described exemplary embodiments are intended to assist the understanding of the invention, and are not intended to limit the scope of the invention in any way.

Embodiment 1

Firstly, an IC tag was produced. The materials used for this will now be described.

The IC chip used was a μ-Chip from Hitachi, Ltd. that was a both-sided electrodes chip having an external electrode formed on the front and the reverse side thereof.

The transmitting/receiving antenna was formed from aluminum foil having a length of 10 μm placed over a PET (polyethylene terephthalate) film of 50 μm in length, with a T-shaped slit 2.4 mm long and 0.3 mm wide etched into the aluminum foil. The transmitting/receiving antenna was 4 mm long and 2.5 mm wide.

For the short circuit board connecting the both-sided electrodes μ-Chip with the transmitting/receiving antenna a tape was used consisting of aluminum foil 10 μm wide placed over PET film 50 μm wide. The tape was 1.2 mm wide and was cut to 3 mm. The connecting material was provided by an anisotropic conductive adhesive film (product name AC-2052P by Hitachi Kasei Polymer Co. Ltd).

Next, after successively laying the anisotropic conductive adhesive film, the both-sided electrodes chip, anisotropic conductive adhesive film and the short circuit board in the required positions for the transmitting/receiving antenna, pressure was applied under heated conditions to obtain the IC tag having the mounting configuration as shown in FIG. 9.

On the other hand, over the end surface of that side of the tubular container of polyvinyl chloride resin having a inner diameter of 2.5 mm and a length of 120 mm forming the side having the sealing cap, aluminum foil 2 mm wide, 50 mm long and 10 μm thick was applied via tape having adhesive both sides (Hibon 11-583 by Hitachi Kasei Polymer Co. Ltd.) forming the tubular container with second transmitting/receiving antenna attached.

Thereafter, one end of the tubular container with antenna attached was sealed by packing therein in succession, a knit braided cotton plug 6 mm long, an IC tag constructed according to the above described process, white powder and a knit braided cotton plug 6 mm long. The appropriate amount of white powder required to tightly pack the IC tag was used.

A tubular container with IC tag provided therein was obtained according to the above described processes.

In order to test the IC tag of the tubular container with the IC tag mounted therein water was poured in the container and after the inlet was fuse sealed shut an IC tag reader was used (from Sekonic Corporation, a Handy Reader R001M, output 10 mW/MHz, 1 batch circularly polarized antenna) to read the information inside the IC tag. With a distance of not more than 2 cm between the IC tag and the reader or when the tag and the reader were positioned such that the center of the antenna was within a 2 cm radial range from the center of the IC tag, the information from the tag could be read in a moment.

Embodiment 2

Firstly, an IC tag was produced according to the same procedures as those used for the IC tag of the first embodiment.

Next, silver wire having a diameter of 30 μm and a length of 50 mm was placed over the surface of a tubular container of polyvinyl chloride resin, 2.5 mm in diameter and 120 mm long, while tape having adhesive on one side thereof was wound around over the silver wire to produce a tubular container with a second transmitting/receiving antenna attached.

Then, a sealing cap with IC tag embedded was formed at the end on one side of the tubular container with IC tag attached using the same procedures as were used for the first embodiment.

The tubular container with IC tag therein was obtained according to the above described procedures.

In order to test the IC tag of the tubular container with the IC tag mounted therein water was poured in the container and after the inlet was fuse sealed shut an IC tag reader was used (from Sekonic Corporation, a Handy Reader R001M, output 10 mW/MHz, 1 patch circularly polarized antenna) to read the information inside the IC tag. With a distance of not more than 2 cm between the IC tag and the reader or when the tag and the reader were positioned such that the center of the antenna was within a 2 cm radial range from the center of the IC tag, the information from the tag could be read in a moment.

Embodiment 3

Firstly, an IC tag was produced according to the same procedures as those used for the IC tag of the first embodiment.

Next, aluminum foil 2 mm wide, 50 mm long and 10 μm thick was adhered using an adhesive agent (product name YA180 by Hitachi Kasei Polymer Co. Ltd.) over the surface of a tubular container of polyvinyl chloride resin, 2.5 mm in diameter and 120 mm long to produce a tubular container with second transmitting/receiving antenna attached.

Then, a sealing cap with IC tag embedded was formed at the end on one side of the tubular container with IC tag attached using the same procedures as were used for the first embodiment.

The tubular container with IC tag therein was obtained according to the above described procedures.

In order to test the IC tag of the tubular container with the IC tag mounted therein water was poured in the container and after the inlet was fuse sealed shut an IC tag reader was used (from Sekonic Corporation, a Handy Reader R001M, output 10 mW/MHz, 1 batch circularly polarized antenna) to read the information inside the IC tag. With a distance of not more than 2 cm between the IC tag and the reader or when the tag and the reader were positioned such that the center of the antenna was within a 2 cm radial range from the center of the IC tag, the information from the tag could be read in a moment.

Embodiment 4

Firstly, an IC tag was produced according to the same procedures as those used for the IC tag of the first embodiment.

Next, to produce a tubular container with second transmitting/receiving antenna attached, over the surface of a tubular container of polyvinyl chloride resin, 2.5 mm in diameter and 120 mm long silver paste was applied so as to be 2 mm wide, 50 mm long and 20 μm thick, and then hardened.

Then, a sealing cap with IC tag embedded was formed at the end on one side of the tubular container with IC tag attached using the same procedures as were used for the first embodiment.

The tubular container with IC tag therein was obtained according to the above described procedures.

In order to test the IC tag of the tubular container with the IC tag mounted therein water was poured in the container and after the inlet was fuse sealed shut an IC tag reader was used (from Sekonic Corporation, a Handy Reader R001M, output 10 mW/MHz, 1 batch circularly polarized antenna) to read the information inside the IC tag. With a distance of not more than 2 cm between the IC tag and the reader or when the tag and the reader were positioned such that the center of the antenna was within a 2 cm radial range from the center of the IC tag, the information from the tag could be read in a moment.

Embodiment 5

Firstly, an IC tag was produced according to the same procedures as those used for the IC tag of the first embodiment.

Next, to produce a tubular container with second and third transmitting/receiving antennas attached, over the surface at the other end from the side at which the sealing cap is formed on a tubular container of polyvinyl chloride resin, 2.5 mm in diameter and 120 mm long, silver paste was applied so as to be 2 mm wide, 50 mm long and 20 μm thick, and then hardened.

Then, a sealing cap with IC tag embedded was formed at the end on one side of the tubular container with IC tag attached using the same procedures as were used for the first embodiment.

The tubular container with IC tag therein was obtained according to the above described procedures.

In order to test the IC tag of the tubular container with the IC tag mounted therein water was poured in the container and after the inlet was fuse sealed shut an IC tag reader was used (from Sekonic Corporation, a Handy Reader R001M) to read the information inside the IC tag. With a distance of not more than 2 cm between the IC tag and the reader or when the tag and the reader were positioned such that the center of the antenna was within a 2 cm radial range from the center of the IC tag, the information from the tag could be read in a moment.

Then, the part of the container that had been fused sealed was cut with pincers and starting from the end opposite that end into which water had entered the sealing cap was pushed using a fine rod to the area at the other end of the container thereby forcing the water out. Under these conditions an IC tag reader was used (from Sekonic Corporation, a Handy Reader R001M, output 10 mW/MHz, 1 batch circularly polarized antenna) to read the information inside the IC tag. With a distance of not more than 2 cm between the IC tag and the reader or when the tag and the reader were positioned such that the center of the antenna was within a 2 cm radial range from the center of the IC tag, the information from the tag could be read in a moment.

COMPARATIVE EXAMPLE 1

Firstly, an IC tag was produced according to the same procedures as those used for the IC tag of the first embodiment.

Next, at one end of a tube made of polyvinyl chloride resin with no antenna formed thereon a sealing cap with IC tag embedded therein was formed according to the same procedures as those used with respect to embodiment 1.

The tubular container with IC tag therein was obtained according to the above described procedures.

In order to test the IC tag of the tubular container with the IC tag mounted therein water was poured in the container and after the inlet was fuse sealed shut an IC tag reader was used (from Sekonic Corporation, a Handy Reader R001M, output 10 mW/MHz, 1 batch circularly polarized antenna) to read the information inside the IC tag, however no information could be read.

Then, an IC tag reader (an MRJ300, output 300 mW by Hitachi Kokusai Electric Inc.) with ceramic chip antenna attached (a YCE-5223 by Yokowo Co., Ltd.) was used to read the information recorded in the IC tag. Only with a distance of not more than 5 mm between the IC tag and the reader or when the tag and the reader were positioned such that the center of the antenna was within a 3 mm radial range from the center of the IC tag could the information from the tag be read.

The results obtained from each of the embodiments and the comparative example are shown in Table 1. Although not detailed in the above description, the results for embodiments 1-5 are shown also with readings that could be obtained using an IC tag reader (an MRJ300, output 300 mW by Hitachi Kokusai Electric)) with ceramic chip antenna (a YCE-5223 by Yokowo Co. Ltd.)) attached.

TABLE 1

| | Reader | | | |
|---|---|---|---|---|
| Type | R001M | | MRJ300 | |
| Output | 100 mW/MHz | | 300 mW | |
| Antenna | 1 batch circularly polarized | | Ceramic chip antenna | |
| Readability | Read distance | Read range | Read distance | Read range |
| Embodiment 1 | 20 mm | Radial 20 mm | 20 mm | Radio 5 mm |
| Embodiment 2 | 20 mm | Radial 20 mm | 20 mm | Radial 5 mm |
| Embodiment 3 | 20 mm | Radial 20 mm | 20 mm | Radial 5 mm |
| Embodiment 4 | 20 mm | Radial 20 mm | 20 mm | Radial 5 mm |
| Embodiment 5 | 20 mm | Radial 20 mm | 20 mm | Radial 5 mm |
| Comparative example 1 | No reading | No reading | 5 mm | Radial 3 mm |

The invention claimed is:

1. A tubular container that enables identification of an individual container and that has an IC tag for individual identification, comprising:
   a tubular container of resin;
   a sealing cap movable in the tubular container;
   an IC tag embedded in the sealing cap and comprising an IC chip and a first transmitting/receiving antenna that mounts the IC chip;
   and a second transmitting/receiving antenna fixed on the surface of the tubular container, the second transmitting/receiving antenna being electrically coupled to the first transmitting/receiving antenna but not electrically connected thereto, the second transmitting/receiving antenna being electrically separated from the IC chip.

2. The tubular container enabling individual identification according to claim 1 wherein the IC tag has a maximum length of 15 mm.

3. The tubular container enabling individual identification according to claim 1 wherein the length of the second transmitting/receiving antenna is within a range of 30 mm-60 mm.

4. The tubular container enabling individual identification according to claim 1 wherein the second transmitting/receiving antenna is metallic film fixed to the tubular container.

5. The tubular container enabling individual identification according to claim 1 wherein the second transmitting/receiving antenna is a metallic wire fixed to the tubular container.

6. The tubular container enabling individual identification according to claim 1 wherein the second transmitting/receiving antenna is a conductive, hardened paste formed on the surface of the tubular container.

7. The tubular container enabling individual identification according to claim 1 wherein the sealing cap is comprised of a fiber part and a powder part.

8. The tubular container enabling individual identification according to claim 1 wherein the sealing cap is a foam resin.

9. The tubular container enabling individual identification according to claim 1 wherein the outer diameter of the tubular container is not more than 3 mm.

10. The tubular container enabling individual identification according to claim 1 wherein the material from which the tubular container is made is any from among polyvinyl chloride resin, polypropylene resin, polyethylene resin or polyester resin.

11. The tubular container enabling individual identification according to claim 1 wherein the IC tag operates on a carrier wave of 2.45 GHz.

12. The tubular container enabling individual identification according to claim 1 wherein the IC tag comprises an IC chip having an external electrode formed on each surface of the pair of facing surfaces, a first transmitting/receiving antenna having a T-shaped slit formed therein, and a short circuit board electrically connecting the IC chip and the first transmitting/receiving antenna.

13. The tubular container enabling individual identification according to claim 1 stored in liquid nitrogen.

14. The tubular container enabling individual identification according to claim 1 wherein a liquid is stored in the tubular container, and said liquid is seminal fluid of a domestic animal.

15. The tubular container enabling individual identification according to claim 1 wherein there is a third transmitting/receiving antenna fixed on the surface of the tubular container.

16. The tubular container enabling individual identification according to claim 15, wherein the third transmitting/receiving antenna forms an electromagnetic coupling with the first transmitting/receiving antenna, when the sealing cap is moved in the tubular container.

17. The tubular container enabling individual identification according to claim 16, wherein the electromagnetic coupling of the first and third transmitting/receiving antennas is by static electricity.

18. The tubular container enabling individual identification according to claim 1, wherein the electrical coupling of the first transmitting/receiving antenna and the second transmitting/receiving antenna arises due to static electricity occurring between the two antennas.

19. The tubular container enabling individual identification according to claim 1, wherein the electrical coupling is an electromagnetic coupling between the two antennas.

20. The tubular container enabling individual identification according to claim 1, wherein the second transmitting/receiving antenna is fixed to a surface of the tubular container.

21. The tubular container enabling individual identification according to claim 1, wherein said second transmitting/receiving antenna is fixed on the outer surface of the tubular container.

* * * * *